United States Patent
Burgoyne

(10) Patent No.: US 6,972,329 B2
(45) Date of Patent: Dec. 6, 2005

(54) MATERIALS AND METHODS FOR RELEASING GENETIC MATERIAL

(75) Inventor: Leigh Alexander Burgoyne, Mitchum (AU)

(73) Assignee: Whatman, Inc., Newton, MA (US)

( * ) Notice: Subject to any disclaimer, the term of this patent is extended or adjusted under 35 U.S.C. 154(b) by 0 days.

(21) Appl. No.: 10/494,885

(22) PCT Filed: Nov. 13, 2002

(86) PCT No.: PCT/US02/36483

§ 371 (c)(1),
(2), (4) Date: May 7, 2004

(87) PCT Pub. No.: WO03/044211

PCT Pub. Date: May 30, 2003

(65) Prior Publication Data

US 2004/0234994 A1    Nov. 25, 2004

Related U.S. Application Data

(60) Provisional application No. 60/336,067, filed on Nov. 15, 2001.

(51) Int. Cl.⁷ .......................................... C07H 21/00
(52) U.S. Cl. ................... 536/25.4; 435/305.3
(58) Field of Search ..................... 536/25.4; 435/305.3

(56) References Cited

U.S. PATENT DOCUMENTS

| 4,563,417 A | 1/1986 | Albarella et al. ............... 435/6 |
| 4,743,535 A | 5/1988 | Carrico ........................... 435/6 |
| 5,525,463 A * | 6/1996 | Zolg ............................... 435/6 |
| 5,756,126 A | 5/1998 | Burgoyne |
| 5,807,527 A | 9/1998 | Burgoyne |
| 5,972,386 A | 10/1999 | Burgoyne |
| 6,294,203 B1 | 9/2001 | Burgoyne |

FOREIGN PATENT DOCUMENTS

| WO | WO 90/03959 | 4/1990 | ........... C07B 63/00 |
| WO | WO 96/09315 A | 3/1996 | |
| WO | WO 00/66606 A | 11/2000 | |
| WO | WO 03/016546 A | 2/2003 | |

OTHER PUBLICATIONS

Arthur D. Little, Inc., "Methylene Blue", CAS No. 61-73-4/7220-79-3, Nov. 30, 1990.

* cited by examiner

*Primary Examiner*—James Ketter
(74) *Attorney, Agent, or Firm*—David G. Conlin; Kathryn A. Piffat; Edwards & Angell, LLP

(57) ABSTRACT

The invention provides methods for isolating and releasing genetic material from a solid medium, such as a DNA array, a filter, a card, or a multiple-well plate, using a wash solution comprising a photolytic agent, followed by subsequent exposure to a light source to release the genetic material, such as genomic DNA. The invention also includes devices and kits for practicing these methods.

51 Claims, 2 Drawing Sheets

Each track (T1-10) is a test of a single solution used to wash bloodstained FTA which was then irradiated as-is and DNA eluted.
T1-T4 & T6-T9 are a 0,5,10,20 ug MeBlue series.
T5 and T10 are 20ug MeBlue but with twice light.
The two panels are tests of SDS as a cofactor.
Top panel is +SDS, bottom panel is -SDS

MATERIALS AND METHODS FOR RELEASING GENETIC MATERIAL

CROSS-REFERENCES TO RELATED APPLICATIONS

The present application is a 35 U.S.C. §371 national stage of PCT application PCT/US2002/036483, filed Nov. 13, 2002, which claims priority of U.S. Provisional Application Ser. No. 60/336,067, filed Nov. 15, 2001, the disclosures of all of which are incorporated herein by reference.

FIELD OF THE INVENTION

The present invention pertains to isolating, storing, and releasing genetic material. The invention provides for a device, method and kit for controllably releasing and recovering genetic material stored on solid media.

BACKGROUND OF THE INVENTION

Genetic material in blood samples is used for the purposes of monitoring and diagnosing genetic diseases and blood-borne parasitic diseases such as malaria. Genetic material can further be used for determining paternity and monitoring other unusual cell populations in blood and other fluids.

Analysis of genetic material can be achieved through numerous techniques and utilizes various materials. Generally, these techniques and methods involve the initial collection of the genetic material, storage of the genetic material and then subsequent analysis of the genetic material.

Various materials and solid media have been and continue to be utilized to provide a base for performing any desired analysis of the genetic material. Those materials include, for example, filter paper or FTA™-coated materials originally developed by researchers at Flinders University, Australia. In particular, FTA™-coated materials have been successfully utilized for preparing all types of genetic material for subsequent genetic analysis. Genetic material prepared using FTA™-coated materials and FTA™ techniques yields highly purified material bound to the cellulosic base filter for the duration of various subsequent applications and amplification reactions. FTA™-coated base filter materials include, but are not limited to Whatman cellulosic BFC-180, 31-ET, glass microfibers, and other similar filter materials known to those of skill in the art.

Genetic material can be purified from FTA™-coated material and then eluted from the filter using a combination of water, dilute organic acids such as acetic acid, and elevated temperatures. The released genetic material is a soluble fragment of varying length that is suitable for a wide variety of amplification and detection methodologies. The elution of the genetic material is important in applications that would not be possible if the genetic material remained bound to the FTA™-coated material. As previously mentioned, FTA™ coating can be done on other filter membrane materials additionally including, but not limited to GF/F, GF/B, QMB, Anopore, alumina, GF/M, magnetic impregnated, meltblown polymerics, and surface modified polymerics. These filter membrane materials can yield superior binding capacity, ease of elution, and extended storage of genetic material.

High molecular weight genetic material does not release well from any media. Specifically, human DNA is composed of enormously long molecules which need to be disassembled to form an optimal size for reliable, repeatable analysis and applications. Although there are methods, such as the use of photolytic agents, to disassemble genetic material, there is no suitable method of controlling and managing genetic material fragment sizes, processing genetic material on solid media, or controllably releasing genetic material from solid media.

Application of genomic DNA to DNA arrays requires high concentrations of DNA fragments of well-controlled sizes for its process controllability and repeatability. Genomic DNA of humans comprises enormously long molecules that must be broken or cut to an optimal size for reliable and repeatable applications. Photolysis is a suitable method of controlling DNA breakage in a robotic environment on a near-white, translucent medium like washed FTA™ with DNA on it. Light application is simply programmable by the programmed switching of a laser or other light source, for times that can be controlled down to microsecond intervals. However, photolysis is not very applicable to crude blood lysates, because the dark-brown-red color interferes with light transmission and thus delivery to the dye-DNA complex. Thus, photolytic agents have not been used in the context of managing DNA fragment sizes while DNA is being processed on solid media, or for the release of DNA from solid media.

The alternative methods of breaking DNA in colored lysates involve intense sound waves that have transmission and safety problems; mechanical methods that are dirty and not readily automatable; or chemical methods that are either disadvantageously complex (acid-base washes) or intrinsically unreliable (e.g., oxidizing agents) in a protein-rich environment of a crude lysate.

This controllability aspect is important as it means that the simple application of crude blood lysates to chips or arrays cannot deliver DNA of defined and controllable size to the chip surface. Therefore, a DNA processing step that also controls DNA size would be highly desirable.

These difficulties apply not only to FTA™ media, but also to any process that binds and releases DNA from a medium. For example, silica with chaotropic agents or DNA-processing media with a low positive charge also have the persistent problems that arise from the fact that very high molecular weight DNA does not release well from any medium.

SUMMARY OF THE INVENTION

In accordance with the present invention, there is provided a method, device, and kit for releasing genetic material bound and stored on any dry solid medium.

In one aspect, the present invention provides a method for releasing genetic material from a solid medium, wherein the method comprises:
  a. providing a solid medium comprising a matrix comprising genetic material;
  b. washing the solid medium, under conditions of limited light or in the dark, with a wash solution comprising:
     i. a buffer; and
     ii. a photolytic agent;
  c. exposing the washed solid medium to a light source to release the genetic material; and
  d. eluting the released genetic material from the solid medium.

In another aspect, the present invention provides a method for isolating genetic material from a biological sample, wherein the method comprises:
  a. applying the biological sample comprising genetic material to a solid medium comprising a matrix;
  b. retaining the genetic material with the solid medium;

c. washing the solid medium, under conditions of limited light or in the dark, with a wash solution comprising:
   i. a buffer; and
   ii. a photolytic agent;
d. removing at least a portion of the non-genetic components of the biological sample from the solid medium;
e. exposing the washed solid medium to a light source to release the genetic material; and
f. eluting the released genetic material from the solid medium.

In another aspect, the present invention provides a method for isolating genetic material from a biological sample, wherein the method comprises:
a. providing a dry solid medium comprising a matrix, having a composition sorbed thereto, wherein the composition comprises:
   i. a weak base;
   ii. a chelating agent; and
   iii. an anionic detergent or surfactant;
b. applying the biological sample comprising genetic material to the solid medium;
c. retaining he genetic material with the solid medium;
d. washing the solid medium, under conditions of limited light or in the dark, with a wash solution comprising:
   i. a buffer;
   ii. a co-releasing agent; and
   iii. a photolytic agent;
e. removing at least a portion of the non-genetic components of the biological sample from the solid medium;
f. exposing the washed solid medium to a light source to release the genetic material; and
g. eluting the released genetic material from the solid medium.

In another aspect, the present invention also provides a device for isolating genetic material from a biological sample, wherein the device comprises:
a. a solid medium comprising a matrix;
b. a composition sorbed to the matrix, wherein the composition comprises:
   i. a weak base;
   ii. a chelating agent; and
   iii. an anionic detergent or surfactant;
c. a covering capable of limiting exposure of the solid matrix to light; and
d. a light source capable of activating a photolytic agent to release genetic material from the solid matrix.

In another aspect, the present invention provides a device for isolating genetic material from a biological sample, wherein the device comprises:
a. a DNA array or a multiple-well plate;
b. a covering capable of limiting exposure of the solid matrix to light; and
c. a light source capable of activating a photolytic agent to release genetic material from the solid matrix.

In another aspect, the present invention also provides a kit for isolating genetic material, wherein the kit comprises:
a. a solid medium comprising a matrix;
b. a composition sorbed to the matrix, wherein the composition comprises:
   i. a weak base;
   ii. a chelating agent; and
   iii. an anionic detergent or surfactant; and
c. a wash solution comprising:
   i. a buffer; and
   ii. a photolytic agent.

In another aspect, the present invention provides a kit for isolating genetic material, wherein the kit comprises:
a. a DNA array or multiple-well plate; and
b. a wash solution comprising:
   i. a buffer; and
   ii. a photolytic agent.

DETAILED DESCRIPTION OF THE INVENTION

Figure 1:
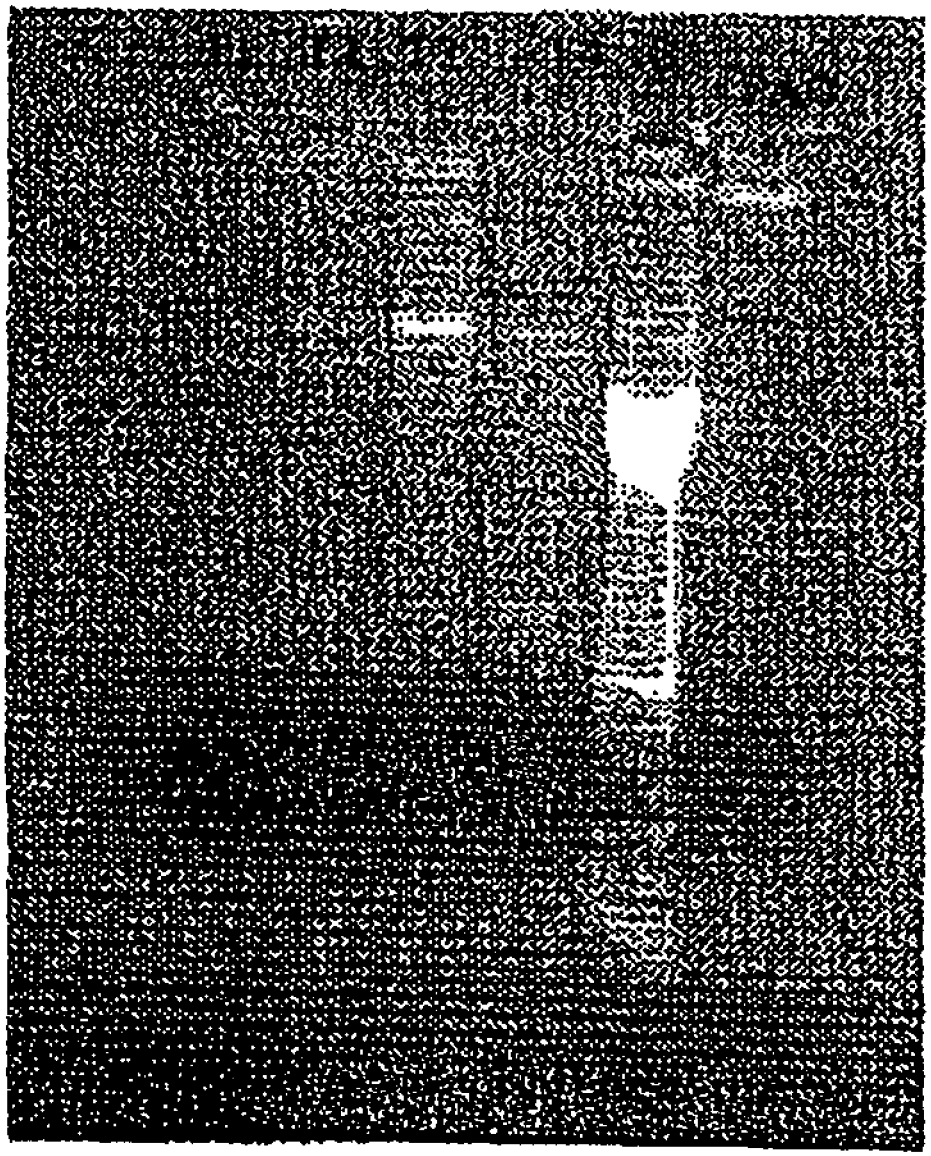
FIG. 1 is a photograph of an agarose gel comparing the effects of different solutions on the solid release of DNA from DNA processing medium. T1=2 mM EDTA alone. T2=2 mM EDTA with methylene blue. T3=2 mM EDTA, 50 $\mu$m Methylene blue, 1% sodium dodecyl sulfate (SDS). T4=2 mM EDTA, 50 $\mu$M methylene blue, polyacrylate. S=standard ladder (100 bp ladder from Amersham Pharmacia Biotech, product no 27-4001). PAC=polyacrylate alone.

Generally, the present invention provides a device, method and kit thereof regarding the controllable release of genetic material from solid media. While specific embodiments are disclosed herein, they are not exhaustive and can include other suitable designs utilizing filters, FTA™-coated materials, silica with chaotropic agents, DNA-processing media with a low positive charge, and any other solid media that bind genetic materials, which are known to those of skill in the art. Examples of useful media include, but are not limited to, those described by U.S. Pat. No. 5,756,126 (May 26, 1998), U.S. Pat. No. 5,807,527 (Sep. 15, 1998), and U.S. Pat. No. 5,972,386 (Oct. 26, 1999), the disclosures of which are incorporated herein by reference.

Moreover, such designs vary in terms of the photolytic agents used, which include, but are not limited to, hematoporphyrin, imidazole, methylene blue, riboflavin, ethidium, and any other agent that absorbs light known to those of skill in the art. Additionally, light sources and the exposure time to the light sources therein can vary. Various light sources include, but are not limited to incandescent lamps, fluorescent lamps, quartz lamps, ultraviolet lamps, heat lamps, laser beams of appropriate spectra, and any other strong light source known to those of skill in the art. Basically, any differing design, process, structure and composite materials known to those skilled in the art can be utilized without departing from the spirit of the present invention.

The present invention can be utilized in, but not limited to, applications that involve direct application of genomic material to genetic arrays or "chips," and those that involve getting relatively large amounts of genetic material off of media in multiple-well analytical systems, such as those used for survey purposes (e.g., surveys of single nucleotide polymorphisms (SNP) for medical purposes). Moreover, in order to facilitate the release of the genetic material, the principles disclosed herein could be used to modify the substrate binding the genetic material, rather than modifying the genetic material itself.

The present invention utilizes various photolytic agents. There can be both primary and secondary photolytic agents. Primary photolytic agents absorb light and include, but are not limited to hematoporphyrin, imidazole, methylene blue, riboflavin, ethidium, and any other agent that absorbs light known to those of skill in the art. Secondary photolytic agents on the other hand, affect the pathway of energy delivery to the genetic material and also affect the energy yield from the primary photolytic agents. Furthermore, these agents manipulate the ratio of genetic material breakage to genetic material damage. Secondary photolytic agents include, but are not limited to, EDTA (made from disodium ethylenediaminetetra-acetate-$2H_2O$), imidazole, and any other similar agent that affects energy delivery and yield known to those of skill in the art.

In one embodiment, the present invention provides a method for isolating genetic material from a biological sample, wherein the method comprises:
a. applying the biological sample comprising genetic material to a solid medium comprising a matrix;
b. retaining the genetic material with the solid medium;
c. washing the solid medium, under conditions of limited light or in the dark, with a wash solution comprising:
    i. a buffer; and
    ii. a photolytic agent;
d. removing at least a portion of the non-genetic components of the biological sample from the solid medium;
e. exposing the washed solid medium to a light source to release the genetic material; and
f. eluting the released genetic material from the solid medium.

In another embodiment, the present invention provides a method for isolating genetic material from a biological sample, wherein the method comprises:
a. providing a dry solid medium comprising a matrix, having a composition sorbed thereto, wherein the composition comprises:
    i. a weak base;
    ii. a chelating agent; and
    iii. an anionic detergent or surfactant;
b. applying the biological sample comprising genetic material to the solid medium;
c. retaining the genetic material with the solid medium;
d. washing the solid medium, under conditions of limited light or in the dark, with a wash solution comprising:
    i. a buffer;
    ii. a co-releasing agent; and
    iii. a photolytic agent;
e. removing at least a portion of the non-genetic components of the biological sample from the solid medium;
f. exposing the washed solid medium to a light source to release the genetic material; and
g. eluting the released genetic material from the solid medium.

Devices and kits enabling the practice of the invention are also envisioned. In one embodiment, the device would include a solid medium, a light source, and a cover, such as a shield or other means to block ambient and other types of light during the washing step. In another embodiment, the kit would provide a solid medium and a wash solution.

In preferred embodiments, the genetic material is DNA, and more preferably, is genomic DNA.

In one particular embodiment, a device is disclosed that includes a dry solid medium and photolytic agents. The dry solid medium includes, but is not limited to FTA™-coated materials, filter paper, and any other similar solid medium known to those of skill in the art. The photolytic agents include, but are not limited to riboflavin, methylene blue, hematoporphyrin, imidazole, ethidium, EDTA, combinations thereof, and any other similar agents that absorb light known to those of skill in the art. The choice of photolytic agents depends on the subsequent analysis and application performed thereafter. For example, if a PCR reaction were to be performed, polyacrylate and polyvinylsulfate would have to be omitted because the PCR reaction is intolerant of excessive polyanions. On the other hand, DNA arrays are very tolerant of non-DNA polyanions and may have improved performance by the presence of these non-DNA polyanions.

In another embodiment, there is provided a dry solid medium and a buffer solution containing photolytic agents. Any appropriate dry solid medium and photolytic agent as those described above can be utilized in this embodiment. Further, the buffer solution includes, but is not limited to 10 mM of sodium phosphate at pH 8.5–9.5, 5 mM of EDTA sodium salt at pH 8.5–9.5, 2 mM sodium EDTA at pH 7.5, or any other suitable buffer solution known to those of skill in the art. In one embodiment, the pH range of the buffer is pH 6.0 to pH 10.0.

In yet another embodiment, a buffer solution containing at least a photolytic agent is provided. Again, any appropriate buffer solution and photolytic agent as those described above can be utilized with this embodiment without departing from the spirit of the present invention.

In any of the previously described embodiments, there can be included releasing agents that aid in detaching genetic material and protein associations. These agents are dispersing agents that include, but are not limited to sodium dodecyl sulfate (SDS) ($C_{12}$), SDS (lauryl; sodium lauryl sulfate), alkyl aryl sulfonates, long chain (fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and any other similar detergents and polyanions known to those of skill in the art. The releasing agents remove or wash away proteins before photolysis occurs. Additionally, the releasing agents solubilize traces of proteins left after photolysis.

Another embodiment of the present invention includes any of the above-mentioned embodiments included into a kit for controllably releasing and recovering genetic material stored on a solid medium. The kit includes a dry solid medium, photolytic agents, a buffer solution, releasing agents, and combinations thereof. Single or multiple solution kits can be created without departing from the spirit of the present invention.

In another embodiment, a method disclosed includes releasing genetic material in a controllable way from FTA™-coated material. Releasing the genetic material must be controlled in order to obtain an optimal segment size of genetic material that will provide reliable performance in their subsequent application. The method basically involves utilizing photolysis to release genetic material from the medium. The method initially involves depositing blood or other biological fluids on FTA™-coated paper, preferably one that is particularly high in SDS. Then, in order to remove non-DNA impurities, the paper is washed with a photolytic buffer reagent solution under dark or subdued ambient light. Controlled DNA fragmentation and release is then accomplished by exposing the washed FTA™-coated paper to an appropriately strong light source.

EXAMPLES

Example 1

One embodiment of the proposed invention is as follows:
An FTA™ paper or another DNA processing medium with very high molecular weight DNA on it of an uncontrolled molecular size.
A solution of a buffer with a low concentration of a photolytic agent such as hematoporphyrin and imidazole or methylene-blue that will cause a high level of double strand breaks. In addition, photolysis may be used on solid media to control molecular size on media that do not release DNA according to size, as does FTA™. For example, silica/chaotropic agent media that releases DNA according to the type of ions present.
A method for using these:
Deposit blood or other biological fluids on an FTA™ paper, by preference, or on another DNA processing medium, one that is particularly high in SDS, in the conventional manner, then wash the reagents and non-DNA impurities out with the photolytic buffer in dark or subdued ambient light. Controlled DNA fragmentation and release is by exposing the washed FTA™ with bound DNA to an appropriately strong light source such as a quartz lamp or a laser beam of appropriate spectrum. The blood pigments and the bulk of the protein should be released when the wash solution is first applied and the DNA released when the light is applied.

Example 2

One example of the components of a single solution for processing DNA and releasing it from DNA processing media.

The solution will contain some or a mixture of all the following components:
(a) A buffer, for example 10 mM sodium phosphate at pH 8.5–9.5. or 5 mM EDTA sodium salt, at pH 8.5–9.5.
(b) A co-releasing agent (optional) that will help detach DNA/protein associations such as sodium polyacrylate or sodium polyvinyl sulfate or sodium dodecyl sulfate at, for example, 500 µg per ml.
(c) A photolytic agent, for example, mixtures of riboflavin, methylene blue, hematoporphyrin and ethidium at, for example, concentrations between 1 µg per ml and 100 µg per ml.

The choice of agents to use in a mix will depend on the application that is to follow. For example, the PCR reaction is intolerant of excessive polyanions so that polyacrylate and polyvinyl sulfate would have to be omitted. However, DNA arrays are potentially very tolerant of non-DNA polyanions and may well be improved in its performance by their presence.

Examples 3 & 4

Summary:
Photolytic release of a large proportion of human DNA of FTA™ can be readily obtained by using a single washing solution with a very low amount of a very safe photolytic agent (methylene blue) and with relatively short light exposure times, ten minutes or less, with conventional strong fluorescent light sources.

The conditions that gave the best results used a blood sample with DNA placed on FTA™-coated material. The FTA™-coated material was then washed (10 ml) with 2 mM EDTA, 5 µm methylene blue, and 1% SDS (to remove PCR interfering species). Finally, the material was subjected to light from a 8 watt fluorescent lamp. In these examples, the DNA was eluted with water.

Technical Comments:
The release of genomic DNA requires mild photolytic breakage with some SDS present. The photolytic agent that achieved the best results of three photolytic agents tested was clearly methylene blue. All discs had blood washed from them with a single solution that contained SDS as a washing agent and the photolytic agent, preferably methylene blue. After blood pigment was washed away, the discs were exposed to the light source for 10 mins and the DNA collected with a small amount of water. The released DNA was in amounts visible to the naked eye when stained on a gel and significantly larger than a kilobase in length, (approximately 10 or more kilobases). The light source that released it was not necessarily a conventional, not particularly powerful source. An intense light at the most efficient action-wavelengths may shorten times, although heating will set natural limits to light intensity, as will be appreciated by one of skill in the art.

Safety Issues:
Minimal. The photolytic agent has been thoroughly assessed by the NIH This is a major report of all its industrial, medical, cancer and other implications, including a long reference list. The report is the NATIONAL TOXICOLOGY PROGRAM, EXECUTIVE SUMMARY OF SAFETY AND TOXICITY INFORMATION; METHYLENE BLUE; CAS Number 61-73-4/7220-79-3; Nov. 30, 1990; Submitted to: NATIONAL TOXICOLOGY PROGRAM; by Arthur D. Little, Inc.

In Examples 3 and 4, the application studied is DNA on DNA chips.

Example 3

This experiment tested methylene blue wash with 5–6 mm discs with dry (24 hours) human blood on FTA™ medium. Each disc was washed with 10 ml of one of the following solutions, prior to illumination:
1. 2 mM EDTA (pH 7.5)
2. 2 mM EDTA (pH 7.5), 50 µM methylene blue
3. 2 mM EDTA (pH 7.5), 50 µM methylene blue, plus 1% SDS
4. 2 mM EDTA (pH 7.5), 50 µM methylene blue, plus 1/20 dilution of stock sodium polyacrylate All discs were irradiated for 10 mins at a distance of 6.5 cm from an 8 watt fluorescent lamp (a relatively low light dosage).

After illumination, the discs were washed twice by centrifugation with 100 µl cold distilled water per wash.

Samples were separated on a 40 ml gel of 1.2% agarose and 1×Tris-borate/EDTA (TBE; 0.045 M Tris-borate/0.001 M EDTA) containing trace ethidium bromide, 6.5 cm long, pH 7.5, run 30 mins at 100 volts, 40 milliAmps. Alcohol precipitated eluents had been resuspended in 15 µl loading solution (0.5 TBE, D20, 0.1% SDS).

FIG. 1 shows the samples as follows:

T1=2 mM EDTA alone. T2=2 mM EDTA with 50 µM methylene blue. T3=2 mM EDTA, 50 µm methylene blue, 1% SDS. T4=2 mM EDTA, 50 µM methylene blue, polyacrylate. S=standard ladder (100 bp ladder from Amersham Pharmacia Biotech, product number 27-4001). PAC=polyacrylate alone. (Note the small, but intense, band near the tope of the photograph in the PAC lane.)

The results in FIG. 1 show a strikingly solid release from sample T3 (sample 3 on track 3; methylene blue/EDTA plus SDS). Note the presence of a solid real reptation band running above the resolution of the standard ladder. Most of the DNA is running above the resolution of the standard ladder.

Example 4

As in Example 3, this experiment utilized 5–6 mm discs with dry human blood on FTA™ medium.

Each disc was washed with 10 ml of solution prior to illumination, then illuminated and water eluted as described above.

1. 2 mM EDTA (pH 7.5), 1% SDS (10 mins illumination)
2. 2 mM EDTA (pH 7.5), 1% SDS, 5 μM methylene blue (10 mins illumination)
3. 2 mM EDTA (pH 7.5), 1% SDS, 20 μM methylene blue (10 mins illumination)
4. 2 mM EDTA (pH 7.5), 1% SDS, 50 μM methylene blue (10 mins illumination)
5. 2 mM EDTA (pH 7.5), 1% SDS, 50 μM methylene blue (20 mins illumination.)
6, 2 mM EDTA (pH 7.5) (10 mins illumination)
7. 2 mM EDTA (pH 7.5), 5 μM methylene blue (10 mins illumination)
8. 2 mM EDTA (pH 7.5), 20 μM methylene blue (10 nuns illumination)
9. 2 mM EDTA (pH 7.5), 50 μM methylene blue (10 mins illumination)
10. 2 mM EDTA (pH 7.5), 50 μM methylene blue (20 mins illumination)

All discs were irradiated for 10 mins at a distance of 6.5 cm from an 8 watt fluorescent lamp, except those irradiated for 20 mins, as noted (still a relatively low light dosage).

After illumination, the discs were washed twice by centrifugation with 100 μl cold distilled water.

Samples were separated on a gel comprising 1% agarose and 1×TBE containing trace ethidium bromide at 5 volts/cm for 30 mins with 10 cm tracks in a doublesized gel (20 cm total). Ammonium acetate/alcohol precipitated eluents were resuspended in 15 μl loading solution (0.5 TBE, D20, 0.1% SDS).

Figure 2:
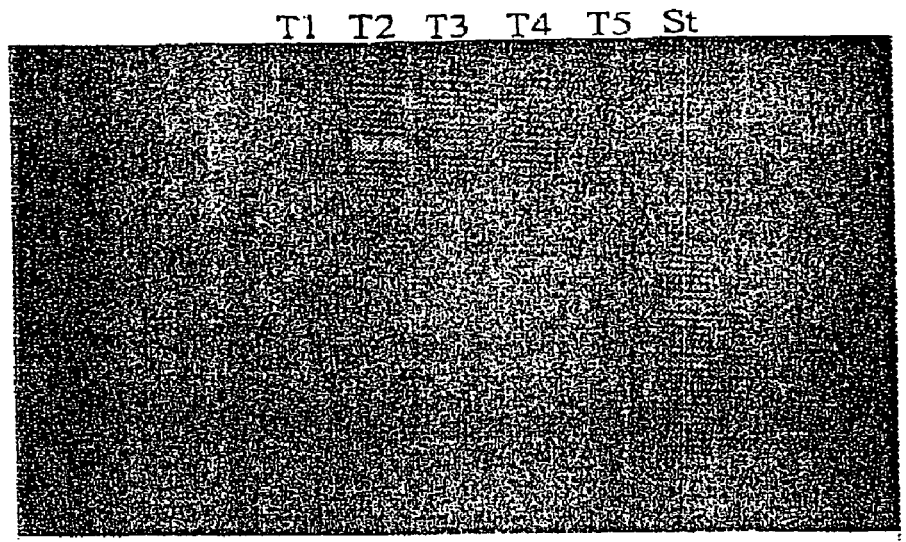
FIG. 2 is a photograph of an agarose gel comparing the effects of different solutions and light exposures on the solid release of DNA from DNA processing medium. In the top row, are samples T1–T5 (tracks of samples 1–5; all containing SDS) and the standard (ST; New England Biolabs 100 bp DNA ladder (Cat. No. N3231S) (sizes=1517, 1200, 1000, 900, 800, 700, 600, 517, 500, 400, 300, 200, 100 bp). In the bottom row, are samples T6–T10 (tracks of samples 6–10; all without SDS). T1–T4 and T6–T9 are a 0, 5, 10, 20, $\mu$g methylene blue series, while T5 and T10 are 20 $\mu$g methylene blue, but with twice the time of light exposure.
Figure 2:
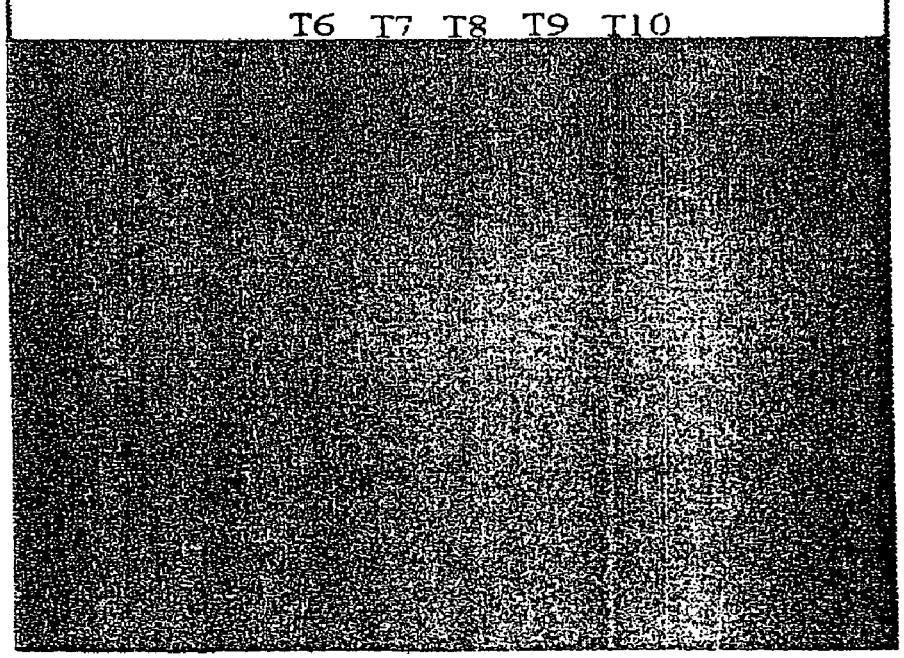

FIG. 2 shows the results of the gel electrophoresis in comparing the effects of the different solutions and light exposures on the solid release of DNA from DNA processing medium. In the top row, are samples T1–T5 (tracks of samples 1–5; all containing SDS) and the standard (ST; New England Biolabs 100 bp DNA ladder (Cat. No. N3231S) (sizes=1517, 1200, 1000, 900, 800, 700, 600, 517, 500, 400, 300, 200, 100 bp). In the bottom row, are samples T6–T10 (tracks of samples 6–10; all without SDS). T1–T4 and T6–T9 are a 0, 5, 10, 20, μg methylene blue series, while T5 and T10 are 20 μg methylene blue, but with twice the time of light exposure.

Conclusions: one preferred treatment is treatment 2, utilizing 5 μm methylene blue in the SDS-containing buffer for 10 mins illumination. Preferably, both SDS and methylene blue are components of the wash solution for efficient release by light after washing. Note that high methylene blue high light causes massive losses (treatment 5) but in the absence of SDS this is the only sample that gives any release at all (treatment 10). There are no signs of very small pieces (less than approx 10 kb) in any track, which suggests that the failures may be due to binding by photolytic reactions, rather than excessive breakage.

Summary of Examples 3 & 4

Photolytic removal of DNA from FTA™ medium only requires washing the blood-loaded FTA™ medium with EDTA/SDS and a very small amount of photolytic agent (methylene blue).

It is practical. In these two trials the elution step utilized water, but other buffers, including, Tris and TE, could be substituted as appreciated by one practicing in the field.

The amount and conditions described above can be modified or adjusted as needed without undue experimentation.

On the basis of its size and the tightness of the bands, the removed DNA should be of high quality based on the presence of large molecular weight bands and the absence of DNA ladders or smearing.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the desired invention, the invention may be practiced otherwise than as specifically described.

What is claimed is:

1. A method for releasing genetic material from a solid medium, wherein the method comprises:
   a. providing a solid medium comprising a matrix comprising genetic material;
   b. washing the solid medium, under conditions of limited light or in the dark, with a wash solution comprising:
      i. a buffer; and
      ii. a photolytic agent;
   c. exposing the washed solid medium to a light source to release the genetic material; and
   d. eluting the released genetic material from the solid medium.

2. The method of claim 1, wherein the genetic material comprises DNA.

3. The method of claim 2, wherein the genetic material comprises genomic DNA.

4. The method of claim 1, wherein the wash solution of step b further comprises a co-releasing agent.

5. The method of claim 1, wherein the solid medium comprises a DNA array or a multiple-well plate.

6. The method of claim 1, wherein the light source is selected from the group consisting of an incandescent lamp, a fluorescent lamp, an ultraviolet lamp, a heat lamp, a quartz lamp, a laser beam, and combinations thereof.

7. The method of claim 1, wherein the buffer has a pH range between 6.0 and 10.0.

8. The method of claim 1, wherein the photolytic agent is selected from the group consisting of hematoporphyrin, imidazole, methylene blue, riboflavin, ethidium, EDTA, polyacrylate, polyvinyl sulfate, and combinations thereof.

9. The method of claim 4, wherein the co-releasing agent is selected from the group consisting of sodium dodecyl sulfate, sodium lauryl sulfate, alkyl aryl sulfonates, long chain (fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and combinations thereof.

10. A method for isolating genetic material from a biological sample, wherein the method comprises:
   a. applying the biological sample comprising genetic material to a solid medium comprising a matrix;
   b. retaining the genetic material with the solid medium;
   c. washing the solid medium, under conditions of limited light or in the dark, with a wash solution comprising:
      i. a buffer; and
      ii. a photolytic agent;
   d. removing at least a portion of the non-genetic components of the biological sample from the solid medium;
   e. exposing the washed solid medium to a light source to release the genetic material; and
   f. eluting the released genetic material from the solid medium.

11. The method of claim 10, wherein the genetic material comprises DNA.

12. The method of claim 11, wherein the genetic material comprises genomic DNA.

13. The method of claim 10, wherein the wash solution of step c further comprises a co-releasing agent.

14. The method of claim 10, wherein the solid medium comprises a DNA array or a multiple-well plate.

15. The method of claim 10, wherein the light source is selected from the group consisting of an incandescent lamp, a fluorescent lamp, an ultraviolet lamp, a heat lamp, a quartz lamp, a laser beam, and combinations thereof.

16. The method of claim 10, wherein the buffer has a pH range between 6.0 and 10.0.

17. The method of claim 10, wherein the photolytic agent is selected from the group consisting of hematoporphyrin, imidazole, methylene blue, riboflavin, ethidium, EDTA, polyacrylate, polyvinyl sulfate, and combinations thereof.

18. The method of claim 13, wherein the co-releasing agent is selected from the group consisting of sodium dodecyl sulfate, sodium lauryl sulfate, alkyl aryl sulfonates, long chain (fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and combinations thereof.

19. A method for isolating genetic material from a biological sample, wherein the method comprises:
   a. providing a dry solid medium comprising a matrix, having a composition sorbed thereto, wherein the composition comprises:
      i. a weak base;
      ii. a chelating agent; and
      iii. an anionic detergent or surfactant;
   b. applying the biological sample comprising genetic material to the solid medium;
   c. retaining the genetic material with the solid medium;
   d. washing the solid medium, under conditions of limited light or in the dark, with a wash solution comprising:
      i. a buffer;
      ii. a co-releasing agent; and
      iii. a photolytic agent;
   e. removing at least a portion of the non-genetic components of the biological sample from the solid medium;
   f. exposing the washed solid medium to a light source to release the genetic material; and
   g. eluting the released genetic material from the solid medium.

20. The method of claim 19, wherein the genetic material comprises DNA.

21. The method of claim 20, wherein the genetic material comprises genomic DNA.

22. The method of claim 19, wherein the solid medium comprises a DNA array or a multiple-well plate.

23. The method of claim 19, wherein the light source is selected from the group consisting of an incandescent lamp, a fluorescent lamp, an ultraviolet lamp, a heat lamp, a quartz lamp, a laser beam, and combinations thereof.

24. The method of claim 19, wherein the buffer has a pH range between 6.0 and 10.0.

25. The method of claim 19, wherein the photolytic agent is selected from the group consisting of hematoporphyrin, imidazole, methylene blue, riboflavin, ethidium, EDTA, polyacrylate, polyvinyl sulfate, and combinations thereof.

26. The method of claim 19, wherein the co-releasing agent is selected from the group consisting of sodium dodecyl sulfate, sodium lauryl sulfate, alkyl aryl sulfonates, long chain (fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and combinations thereof.

27. A device for isolating genetic material from a biological sample, wherein the device comprises:
   a. a solid medium comprising a matrix;
   b. a composition sorbed to the matrix, wherein the composition comprises:
      i. a weak base;
      ii. a chelating agent; and
      iii. an anionic detergent or surfactant;
   c. a covering capable of limiting exposure of the solid matrix to light; and
   d. a light source capable of activating a photolytic agent to release genetic material from the solid matrix.

28. The device of claim 27, wherein the light source is selected from the group consisting of an incandescent lamp, a fluorescent lamp, an ultraviolet lamp, a heat lamp, a quartz lamp, a laser beam, and combinations thereof.

29. A device for isolating genetic material from a biological sample, wherein the device comprises:
   a. a DNA array or a multiple-well plate;
   b. a covering capable of limiting exposure of the solid matrix to light; and
   c. a light source capable of activating a photolytic agent to release genetic material from the solid matrix.

30. The device of claim 29, wherein the light source is selected from the group consisting of an incandescent lamp, a fluorescent lamp, an ultraviolet lamp, a heat lamp, a quartz lamp, a laser beam, and combinations thereof.

31. A kit for isolating genetic material, wherein the kit comprises:
   a. a solid medium comprising a matrix;
   b. a composition sorbed to the matrix, wherein the composition comprises:
      i. a weak base;
      ii. a chelating agent; and
      iii. an anionic detergent or surfactant; and
   c. a wash solution comprising:
      i. a buffer; and
      ii. a photolytic agent.

32. The kit of claim 31, wherein the wash solution of part c further comprises a co-releasing agent.

33. The kit of claim 31, wherein the buffer has a pH range between 6.0 and 10.0.

34. The kit of claim 31, wherein the photolytic agent is selected from the group consisting of hematoporphyrin, imidazole, methylene blue, riboflavin, ethidium, EDTA, polyacrylate, polyvinyl sulfate, and combinations thereof.

35. The kit of claim 32, wherein the co-releasing agent is selected from the group consisting of sodium dodecyl sulfate, sodium lauryl sulfate, alkyl aryl sulfonates, long chain (fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and combinations thereof.

36. A kit for isolating genetic material, wherein the kit comprises:
   a. a DNA array or multiple-well plate, wherein the DNA array or multiple-well plate comprises a dry solid medium comprising:
      i. a matrix; and
      ii. a composition sorbed to the matrix, wherein the composition comprises an anionic surfactant or detergent; and
   b. a wash solution comprising:
      i. a buffer; and
      ii. a photolytic agent.

37. The kit of claim 36, wherein the wash solution of part b further comprises a co-releasing agent.

38. The kit of claim 36, wherein the buffer has a pH range between 6.0 and 10.0.

39. The kit of claim 36, wherein the photolytic agent is selected from the group consisting of hematoporphyrin, imidazole, methylene blue, riboflavin, ethidium, EDTA, polyacrylate, polyvinyl sulfate, and combinations thereof.

40. The kit of claim 37, wherein the co-releasing agent is selected from the group consisting of sodium dodecyl sulfate, sodium lauryl sulfate, alkyl aryl sulfonates, long chain (fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and combinations thereof.

41. The method of claim 1, wherein the solid medium further comprises a dry solid medium comprising a composition sorbed to the matrix, wherein the composition comprises an anionic surfactant or detergent.

42. The method of claim 41, wherein the composition further comprises:
   a. a weak base; and
   b. a chelating agent.

43. The method of claim 42, wherein:
   a. the weak base comprises a Tris base;
   b. the chelating agent comprises ethylenediamine tetraacetic acid (EDTA); and
   c. the anionic surfactant or detergent comprises sodium dodecyl sulfate (SDS).

44. The method of claim 10, wherein the solid medium comprises a dry solid medium further comprising a composition sorbed to the matrix, wherein the composition comprises an anionic surfactant or detergent.

45. The method of claim 44, wherein the composition further comprises:
   a. a weak base; and
   b. a chelating agent.

46. The method of claim 45, wherein:
   a. the weak base comprises a Tris base;
   b. the chelating agent comprises ethylenediamine tetraacetic acid (EDTA); and
   c. the anionic surfactant or detergent comprises sodium dodecyl sulfate (SDS).

47. The device of claim 29, wherein the wherein the DNA array or multiple-well plate comprises a dry solid medium comprising
   i. a matrix; and
   ii. a composition sorbed to the matrix, wherein the composition comprises an anionic surfactant or detergent.

48. The device of claim 47, wherein the composition further comprises:
   a weak base; and
   a chelating agent.

49. The device of claim 48, wherein:
   a. the weak base comprises a Tris base;
   b. the chelating agent comprises ethylenediamine tetraacetic acid (EDTA); and
   c. the anionic surfactant or detergent comprises sodium dodecyl sulfate (SDS).

50. The kit of claim 35, wherein the composition further comprises:
   a. a weak base; and
   b. a chelating agent.

51. The kit of claim 50, wherein:
   a. the weak base comprises a Tris base;
   b. the chelating agent comprises ethylenediamine tetraacetic acid (EDTA); and
   c. the anionic surfactant or detergent comprises sodium dodecyl sulfate (SDS).

* * * * *